(12) United States Patent
Meinert et al.

(10) Patent No.: US 8,661,906 B2
(45) Date of Patent: *Mar. 4, 2014

(54) ULTRASOUND TEST DEVICE WITH IMPROVED ALIGNMENT

(75) Inventors: Damian Meinert, Langenfeld (DE); Reinhard Prause, St. Augustin (DE); Rainer Vierhaus, Puhlheim (DE)

(73) Assignee: GE Sensing & Inspection Technologies GmbH (DE)

( * ) Notice: Subject to any disclaimer, the term of this patent is extended or adjusted under 35 U.S.C. 154(b) by 650 days.

This patent is subject to a terminal disclaimer.

(21) Appl. No.: 12/674,461

(22) PCT Filed: May 30, 2008

(86) PCT No.: PCT/EP2008/056695
§ 371 (c)(1),
(2), (4) Date: Mar. 30, 2010

(87) PCT Pub. No.: WO2009/024365
PCT Pub. Date: Feb. 26, 2009

(65) Prior Publication Data
US 2011/0120224 A1     May 26, 2011

(30) Foreign Application Priority Data

Aug. 20, 2007    (DE) .......................... 10 2007 039 326

(51) Int. Cl.
*G01N 29/00*      (2006.01)
(52) U.S. Cl.
USPC .................................. 73/649; 73/633; 73/644
(58) Field of Classification Search
USPC ............ 73/622, 602, 623, 638, 644, 633, 649
See application file for complete search history.

(56) References Cited

U.S. PATENT DOCUMENTS

| | | | |
|---|---|---|---|
| 2,873,391 A | 11/1955 | Schulze | |
| 3,129,581 A | 4/1964 | Hans-Wilhelm Bande | |
| 3,225,202 A * | 12/1965 | Rich, Jr. et al. | ............... 250/349 |
| 3,257,843 A | 6/1966 | Cowan | |
| 3,420,097 A | 1/1969 | Bettermann et al. | |
| 3,938,371 A | 2/1976 | Dini | |

(Continued)

FOREIGN PATENT DOCUMENTS

| | | |
|---|---|---|
| DE | 2740106 | 3/1979 |
| DE | 2740106 A1 | 3/1979 |

(Continued)

OTHER PUBLICATIONS

International Search Report PCT/EP2008/056695; Dated Oct. 14, 2008.

(Continued)

*Primary Examiner* — J M Saint Surin
(74) *Attorney, Agent, or Firm* — Cantor Colburn LLP

(57) ABSTRACT

The invention relates to an ultrasound inspection device for the inspection of tubular workpieces, where the ultrasound inspection device can be coupled to the workpiece by means of a fluid medium, so that sound emitted from a transducer unit hits an insonification point on the lateral surface of the workpiece, the workpiece and the ultrasound inspection device can be moved relative to each other, and where the transducer unit is pivotable on a pivoting line which corresponds to an arc of a circle whose center is formed by the insonification point.

9 Claims, 2 Drawing Sheets

(56) References Cited

U.S. PATENT DOCUMENTS

| | | |
|---|---|---|
| 3,938,372 A | 2/1976 | Sproule |
| 4,472,975 A | 9/1984 | Beck |
| 5,228,343 A * | 7/1993 | Schoenen et al. ............... 73/644 |
| 5,469,744 A * | 11/1995 | Patton et al. .................... 73/644 |
| 5,473,943 A * | 12/1995 | Schoenen et al. ............... 73/644 |
| 6,257,462 B1 * | 7/2001 | Kelley ........................... 222/456 |
| 6,298,727 B1 | 10/2001 | Fleming et al. |
| 6,298,777 B1 * | 10/2001 | Dubois et al. ................... 101/27 |
| 6,481,290 B1 * | 11/2002 | MacInnis et al. ............... 73/644 |
| 6,916,083 B2 * | 7/2005 | Miller et al. .................... 347/46 |
| 6,945,113 B2 * | 9/2005 | Siverling et al. ............... 73/622 |
| 6,948,369 B2 * | 9/2005 | Fleming et al. ................. 73/588 |
| 7,181,969 B2 * | 2/2007 | Busch et al. .................... 73/618 |
| 7,412,890 B1 * | 8/2008 | Johnson et al. ................ 73/618 |
| 8,042,399 B2 * | 10/2011 | Pasquali et al. ................ 73/623 |
| 2004/0016299 A1 | 1/2004 | Glascock et al. |
| 2007/0038110 A1 * | 2/2007 | Flesch et al. ................... 600/459 |

FOREIGN PATENT DOCUMENTS

| | | |
|---|---|---|
| DE | 2751810 | 5/1979 |
| DE | 2751810 A1 | 5/1979 |
| EP | 0556635 | 8/1993 |
| FR | 1065907 | 5/1954 |
| GB | 2190493 | * 11/1987 |
| JP | 58092949 | 6/1983 |

OTHER PUBLICATIONS

ISR PCTEP2008056696 dtd Oct. 9, 2008.

* cited by examiner

ULTRASOUND TEST DEVICE WITH IMPROVED ALIGNMENT

CROSS REFERENCE TO RELATED APPLICATION

This patent application claims priority to German Patent Application DE 10 2007 039 326.3, filed Aug. 20, 2007 which is hereby expressly incorporated by reference in its entirety.

TECHNICAL FIELD

The present invention relates to an ultrasound inspection device for inspecting tubular workpieces which can be coupled to the workpiece by means of a fluid. In that case, the workpiece or tube rotates about its longitudinal axis and is inspected. Alternatively, however, ultrasound inspection devices which themselves are moving while the workpiece or tube remains stationary are also known. For the purpose of emitting sound, ultrasound inspection device comprise so-called transducer units with a transmitter and, optionally, also a receiver; however, the receiver can also be located elsewhere.

BACKGROUND

The inspection of tubular workpieces is demanding because, among other things, a sufficient and interference-free coupling of the ultrasound inspection device is rather difficult. Moreover, the intensity of the received signals is very much dependent upon the surface geometry, which is the reason why a test probe is actually proposed in DE 27 40 106 which determines the alignment of two other, outer test probes in accordance with the surface geometry of the workpiece to be inspected, by means of a sound attenuation measurement. This device and the underlying method are complex and cost-intensive.

An inspection device for non-destructive inspection is known from DE 27 51 810, in which a total of six test probes, the sound beams of which intersect in a single point, are arranged in an inspecting spider. The sound-transmitting coupling is carried out by supplying water into the plane of contact. It is a drawback of this arrangement that the coupling medium is supplied in an uncontrolled manner; the effort for monitoring the coupling is thus very high. However, it is also a particular drawback that the adaptation to different tube diameters, and also the adjustment of the insonification angle, is laborious.

BRIEF SUMMARY

The disclosure provides an ultrasound inspection device with which an inspection of tubular workpieces is possible that is as quick and exact as possible. In this case, the ultrasound inspection device is supposed to be as simple as possible with regard to construction and operation, and should be capable of being used for different inspection techniques. In particular, maintaining an insonification angle that is as constant as possible is supposed to be easily manageable by the user.

Accordingly, in the ultrasound inspection device according to the invention, the transducer unit can be pivoted exactly to the insonification point on the lateral surface. It is thus achieved that the insonification point on the lateral surface is maintained exactly, even if the transducer unit is pivoted, because the pivoting line corresponds exactly to the arc of a circle whose center is formed by the insonification point on the lateral surface.

The ultrasound inspection device comprises a cluster housing which terminates with a diameter-adapted wear sole on the outer lateral surface of the workpiece, that is, on the tube surface. A chamber for accommodating the coupling medium, preferably water, is thus formed. The chamber is not filled from the top towards the bottom, as is known in the prior art, but rather a filling process is provided which starts from the outer lateral surface of the workpiece. Thus, the fluid is supplied to the chamber close to the outer lateral surface and then rises in the cluster housing. The result of this advantageous supply is that air bubbles that possibly occur rise with the fluid, and are thus discharged significantly faster and without turbulence. This, precisely, is not the case in inspection devices according to the prior art; usually, the fluid flows from above in the opposite direction to the rising air bubbles.

Corresponding fluid inlet openings can be constructionally configured such that the fluid jet is guided through at least one channel perpendicularly onto the tube surface. Starting from the tube surface, the chamber is then evenly flooded in a bubble-free manner from the bottom towards the top, based on the length of the test probe line.

At least one fluid outlet channel serves for venting and draining the chamber and preferably opens laterally of or above the transducer unit, in particular above the test probes on a fluid outlet opening. A formation of air bubbles in front of the transducer unit, that is, between the workpiece and the test probes, can thus be avoided by means of fluid engineering. The number of the fluid outlet channels and fluid outlet openings can be individually adapted to the length of the test probe lines or the number of the individual test probes.

According to the invention, the cluster housing can be designed for a conventional or for phased array technique. A large chamber is also suitable, in particular, for a phased array inspection technique with the so-called paintbrush method within the cluster housing.

In a particularly advantageous embodiment, the cluster housing is divided into a contact body and a transducer unit housing. The contact body adjoins the wear sole, the transducer unit housing contains the oscillating body and is mounted pivotably relative to the contact body. The chamber extends through the contact body into the transducer unit housing. The pivoting line of the transducer unit, in this preferred exemplary embodiment, is formed by the outer contour of the contact body.

Using spacers, an increase in height of the cluster housing and thus, a greater distance of the transducer unit from the lateral surface of the workpiece can be realized. The transducer unit housing is subdivided for this purpose.

Thus, the contact body has a convex curvature in the direction of the transducer unit housing. On its underside, that is, the side which comes into contact with the contact body, the transducer unit housing is introduced with a correspondingly concave curvature.

In order for the inspection setting to be reproducible, the insonification angle can be mechanically fixated in different angular positions, that is, the transducer unit housing can be fixed relative to the contact body.

It has proved to be advantageous if not only a single fluid inlet opening is provided, but if the fluid is introduced into the chamber evenly through several openings.

The wear sole with the concave curvature is configured to be replaceable, so that the inspection device can be adapted to different diameters.

The invention is explained further with reference to the following figures. The exemplary embodiment described therein should be understood merely to be an example, and is not supposed to limit the scope of the invention.

DETAILED DESCRIPTION

Figure 1:
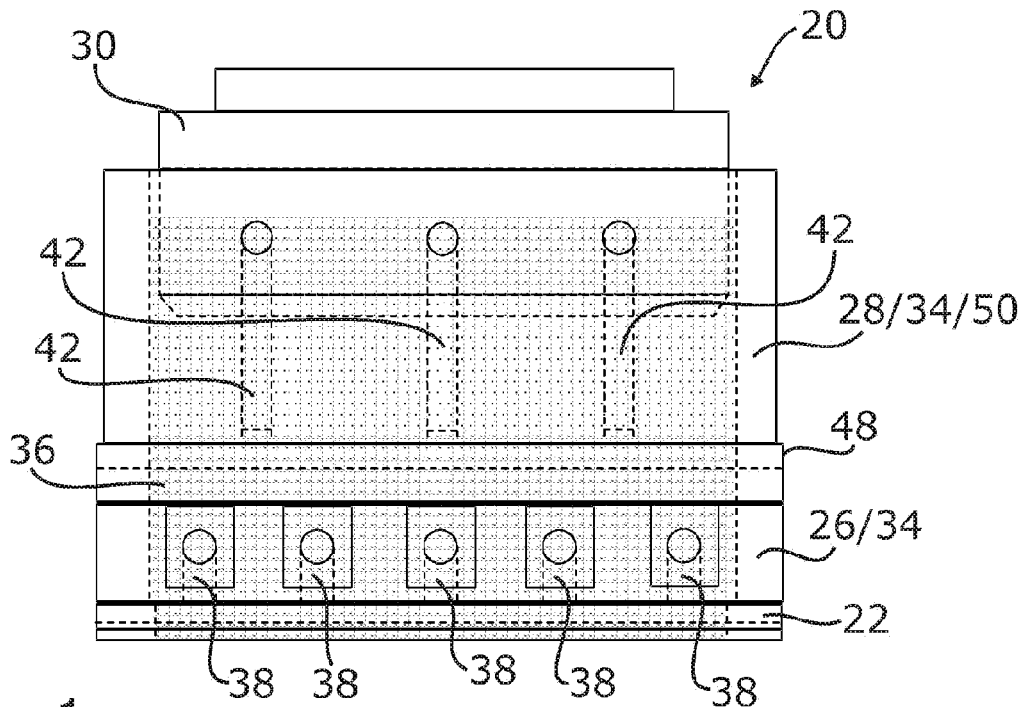
FIG. 1 shows an ultrasound inspection device according to the invention in a frontal view.
Figure 2:
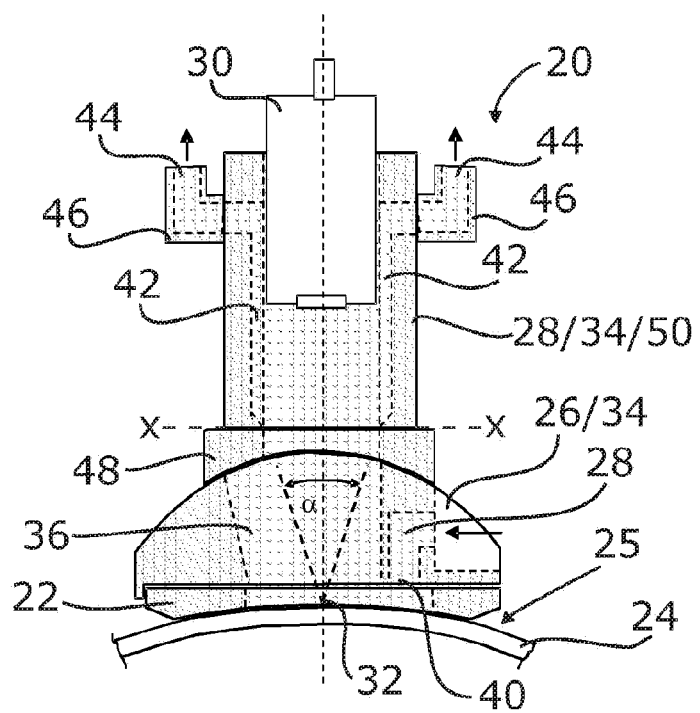
FIG. 2 shows the ultrasound inspection device from FIG. 1 in a lateral view.

FIGS. 1 and 2 show an ultrasound inspection device 20 according to the invention. It has a wear sole 22, which, depending on the diameter of a workpiece 24 to be inspected, has a concave curvature which adjoins the workpiece 24 to be inspected. The wear sole 22 is replaceable, thus, the degree of curvature can be adapted to different tube diameters or outer lateral surfaces 25.

In the exemplary embodiment shown, the wear sole 22 is disposed on a contact body 26 which in turn is adjoined by a transducer unit housing 28. A transducer unit 30 comprising the required transmitter and receiver modules is shown within the transducer unit housing 28. The sound hits an insonification point at an angle α, which is, for example, 19°. The transducer unit housing 28 is configured to be pivotable relative to the contact body 26. For this purpose, in the exemplary embodiment shown, the contact body 26 is configured to be convex on its side facing towards the transducer unit housing 28, whereas the transducer unit housing 28 has a concave curvature corresponding thereto.

The concave and convex curvatures, respectively, of the contact body 26 and of the transducer unit housing 28 are configured such that the pivoting line S-S resulting therefrom corresponds to an arc of a circle, the center of which is formed by the insonification point 32 which lies on the lateral surface 25 of the workpiece 24. In the exemplary embodiment shown, the transducer unit housing 28 stands vertically on the contact body 26; however, it can be pivoted both to the right as well as to the left. The definition of the pivoting line S-S as an arc of a circle of the insonification point 32 has the effect that the sound always exactly hits the insonification point 32 at the same angle α, irrespective of the degree of pivoting (also see FIG. 3).

The contact body 26 and the transducer unit housing 28 form a cluster housing 34 in which a chamber 36 is located. The chamber 36 adjoins the workpiece 24 or is opened in the direction of the workpiece 24 to be able to effect a coupling by means of a fluid.

The chamber 36 can be filled through a fluid inlet channel 38, which, with a fluid inlet opening 40, opens into the chamber 36. The fluid inlet channel 38 is in this case preferably configured such that the fluid is directed as perpendicularly as possible onto the outer lateral surface 25 of the workpiece 24. FIG. 1 illustrates that several fluid inlet channels 38, five in the exemplary embodiment shown, can also be provided. The chamber 36 is flooded via the fluid inlet channels 38, starting from the lateral surface 25 of the workpiece 24; the fluid rises upwards in the chamber 36 and is conducted into fluid outlet channels 42. The fluid outlet channels 42 open into fluid outlet openings 44, which discharge the fluid from the cluster housing 34 and from the ultrasound inspection device 20, respectively. In the exemplary embodiment, chimney-shaped fluid outlet channel ends 46 are provided which convey the fluid away from the transducer unit 30 and out above test probes which are not shown. The fluid outlet channel ends 46 are disposed on the outside of the cluster housing 34 and protrude therefrom. The number and paths of the fluid outlet channels 42 and of the fluid outlet channel ends 46 can be chosen freely, depending on the requirements and the constructional conditions.

Spacers which can be inserted into a divisible cluster housing 34 are not shown. In FIG. 2, in particular, it can be seen that the transducer unit housing 28 is divided into a fitted housing part 48, which fits onto the contact body 26, and an upper housing portion 50 adjoining thereto. These two housing portions 48, 50 are in contact along a parting line x-x. Spacers or elements can, for example, be inserted between the fitted housing portion 48 and the upper housing portion 50, whereby the distance of the transducer unit 30 to the workpiece 24 and to the insonification point 32, respectively, can be varied.

Figure 3:
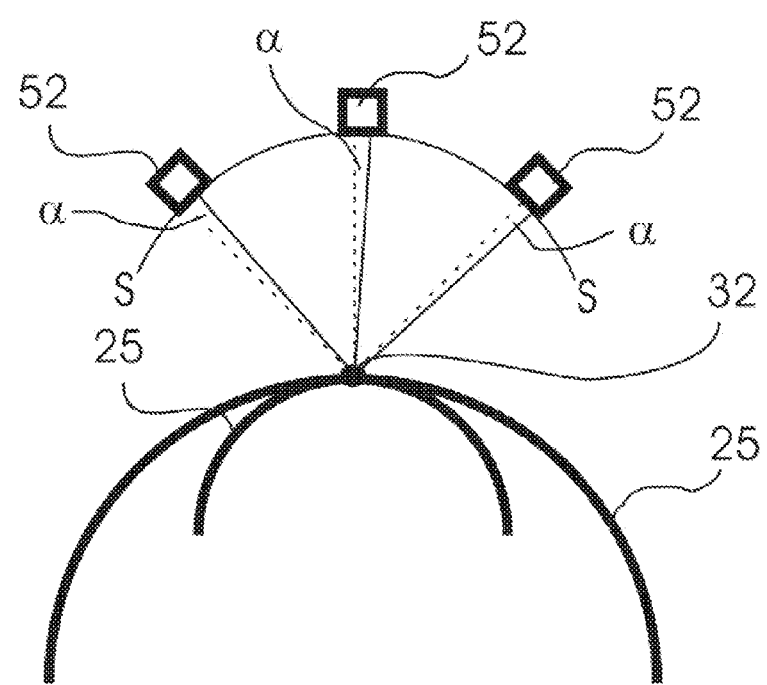
FIG. 3 shows a schematic view of the adjustment of the angle.

FIG. 3 illustrates the geometric interrelations of the angle adjustment according to the invention of the ultrasound inspection device 20. What is shown are outer lateral surfaces 25 of two workpieces 24 with different diameters. The desired insonification point 32 lies on these two outer lateral surfaces 25. Moreover, a test probe 52 is shown in three different positions. Furthermore, the pivoting line S-S, on which the test probe 52 can be pivoted, is drawn in. The center belonging to the pivoting line S-S is the insonification point 32. In every position on the pivoting line S-S, the test probe 52 thus has the same distance and the same angle to the insonification point 32, whereby the inspection of workpieces 24 of different diameters can be carried out quickly and easily while maintaining the desired adjustment angles.

The ultrasound inspection device 20 according to the invention is suitable for realizing various inspection techniques, for example, angled insonification; in addition, the insonification angle is always maintained when different spacers are being used.

The invention claimed is:

1. Ultrasound inspection device for the inspection of tubular workpieces, the ultrasound inspection device comprising:
   a cluster housing divided into a transducer unit housing and a contact body, the contact body adjoining a wear sole configured to place on the outer lateral surface of the workpiece, and the transducer unit housing having a transducer unit and is pivotable relative to the contact body, wherein
   the ultrasound inspection device is configured to couple to the workpiece by means of a fluid medium, so that sound emitted from the transducer unit hits an insonification point on a lateral surface of the workpiece,
   the workpiece and the ultrasound inspection device configured to move relative to each other,
   the transducer unit is pivotable on a pivoting line, which corresponds to an arc of a circle whose center is formed by the insonification point, wherein the transducer unit is configured to fixate in an position relative to the insonification point, and
   the wear sole is configured such that a chamber forms between the workpiece and the transducer unit, and that at least one fluid inlet channel, which, with a fluid inlet opening, opens into the chamber, and at least one fluid outlet channel for venting and draining the chamber, which opens into the chamber, are provided, wherein the mouth of the fluid outlet channel and the fluid outlet channel are configured and disposed such that a filling process of the chamber and of the fluid outlet channel are configured to carry out starting on an outer lateral surface of the workpiece, and then in a rising manner.

2. Ultrasound inspection device according to claim 1, wherein the fluid inlet channel and the fluid inlet opening are configured and disposed such that the fluid is conducted perpendicularly onto the outer lateral surface of the workpiece.

3. Ultrasound inspection device according to claim 1, wherein the fluid outlet channel comprises a fluid outlet opening which, relative to the lateral surface, is disposed above a test probe of the transducer unit.

4. Ultrasound inspection device according to claim 3, wherein the fluid outlet channel comprises a fluid outlet channel end protruding from cluster housing.

5. Ultrasound inspection device according to claim 1, wherein several fluid inlet channels are provided.

6. Ultrasound inspection device according to claim 1, wherein several fluid outlet channels are provided.

7. Ultrasound inspection device according to claim 1, wherein a distance of the transducer unit from the insonification point is configured to change by means of spacers configured to insert into the cluster housing.

8. Ultrasound inspection device according to claim 1, wherein the transducer unit comprises several test probes.

9. Ultrasound inspection device according to claim 8, wherein the chamber has dimensions which permits a phased array inspection technique.

* * * * *